(12) United States Patent
Der Ovanesian

(10) Patent No.: US 8,795,211 B2
(45) Date of Patent: Aug. 5, 2014

(54) PORTABLE AND RECHARGEABLE CAST VENTILATING SYSTEM HAVING A CLIMATE CONTROL ELEMENT

(76) Inventor: Mary Der Ovanesian, Lauderdale, FL (US)

( * ) Notice: Subject to any disclaimer, the term of this patent is extended or adjusted under 35 U.S.C. 154(b) by 161 days.

(21) Appl. No.: 12/426,243

(22) Filed: Apr. 18, 2009

(65) Prior Publication Data
US 2010/0268136 A1    Oct. 21, 2010

(51) Int. Cl.
*A61F 13/04* (2006.01)

(52) U.S. Cl.
USPC .................................. 602/14; 602/2; 602/13

(58) Field of Classification Search
CPC ............................... A61F 13/046; A61F 13/04
USPC ................. 602/2, 5, 13, 14; 607/104, 108
See application file for complete search history.

(56) References Cited

U.S. PATENT DOCUMENTS

| | | | |
|---|---|---|---|
| 3,908,642 A * | 9/1975 | Vinmont | 601/149 |
| 3,998,220 A * | 12/1976 | Cleer et al. | 602/14 |
| 4,308,862 A | 1/1982 | Kalmar | |
| 4,387,710 A | 6/1983 | Beatty | |
| 4,677,970 A | 7/1987 | Green et al. | |
| 4,898,160 A | 2/1990 | Brownlee | |
| 6,120,469 A | 9/2000 | Bruder | |
| 6,416,534 B1 | 7/2002 | Montagnino | |
| 7,022,093 B2 | 4/2006 | Smith et al. | |
| 7,828,757 B2 * | 11/2010 | Blocker | 602/2 |
| 2008/0183115 A1 * | 7/2008 | Pierce | 602/13 |
| 2010/0010408 A1 * | 1/2010 | Linares | 602/14 |

* cited by examiner

*Primary Examiner* — Patricia Bianco
*Assistant Examiner* — Kari Petrik
(74) *Attorney, Agent, or Firm* — Johnson & Martin, P.A.; James David Johnson

(57) ABSTRACT

A portable and rechargeable cast ventilating system adapted for use on casts, the system comprises of a portable fluid flow manipulations device, a manifold collar, and at least one tube. The system is attached to a cast being worn by a user so that each tube is inserted between the cast and the body part of the user being covered by the cast, the manipulation collar is attached to the cast so that the collar operatively connects to the tubes, and the portable fluid flow manipulation device operatively connects to the collar. The system delivers a fluid flow within a cast being worn by the user. The temperature of the fluid flow delivered to areas being covered by the cast might be controlled by a heat transfer element of the fluid flow manipulation device.

17 Claims, 5 Drawing Sheets

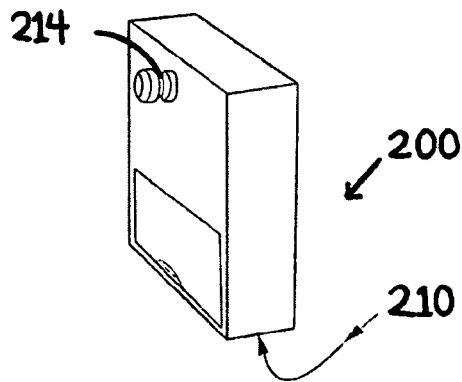
Fig. 5A
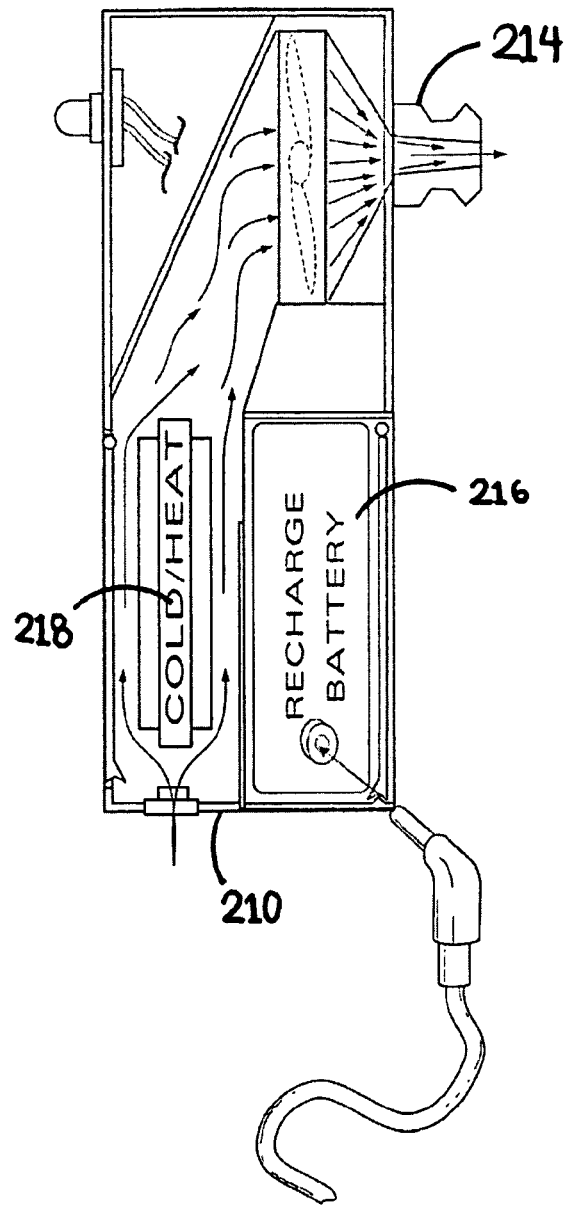
Fig. 5B
Fig. 6

US 8,795,211 B2

PORTABLE AND RECHARGEABLE CAST VENTILATING SYSTEM HAVING A CLIMATE CONTROL ELEMENT

BACKGROUND

The present invention is directed to the field of portable cast ventilating systems adapted for use on casts.

The inventor of the present invention conceived the invention when she suffered a fracture. They treated the fracture by placing a cast over the fracture. She noticed that the cast became increasingly uncomfortable as time passed. The reason that the cast was uncomfortable stemmed from the fact that there was no fluid circulation between the cast and her skin.

Because of the lack of fluid circulation, her body sweated in the areas immediately covered by the cast. The sweating caused her to itch and she devised ways of jabbing things within the cast to somewhat create a fluid flow within the cast and also to scratch the areas not being in contact with a fluid flow.

Another problem she encountered when she used the cast was bacteria build up caused by the lack of fluid circulation that in turn generated an odor.

Stand alone ventilators for casts have been disclosed in U.S. Pat. Nos. 6,120,469; 4,898,160; 4,387,710; 3,998,220; 4,308,862; 7,022,093; 6,416,534 B1; AND 4,677,970. None of the recited patents disclose a portable cast ventilating system having a rechargeable power source and a rechargeable heat transfer element.

For the foregoing reasons, there is a need for a portable cast ventilating system that is portable, that has a rechargeable power source, and that has a rechargeable heating element that is adapted for the use on casts.

SUMMARY

The present invention is directed to a portable cast ventilating system that is portable, that has a rechargeable power source, and that has a rechargeable heating element that is adapted for the use on casts.

A portable and rechargeable cast ventilating system adapted for use on casts, the system comprises of a portable fluid flow manipulations device, a manifold collar, and at least one tube. The system is attached to a cast being worn by a user so that each tube is inserted between the cast and the body part of the user being covered by the cast, the manipulation collar is attached to the cast so that the collar operatively connects to the tubes, and the portable fluid flow manipulation device operatively connects to the collar. The system delivers a fluid flow within a cast being worn by the user. The temperature of the fluid flow delivered might be controlled by a heat transfer element of the fluid flow manipulation device.

An object of the present invention is to provide a portable and rechargeable cast ventilating system adapted for use on casts that will allow users of the system to carry out their normal tasks without having to have the system plugged in.

Another object of the present invention is to provide a portable and rechargeable cast ventilating system adapted for use on casts that will allow a user to control the temperature of the fluid flow delivered to the areas of the user being covered by the cast.

A further object of the present invention is to provide a portable and rechargeable cast ventilating system adapted for use on casts that could be recharged while the user of the system is using the cast.

Still a further object of the present invention is to provide a portable and rechargeable cast ventilating system that will allow a user to minimize the normal odors accumulated within a cast due to use.

DRAWINGS

These and other features, aspects, and advantages of the present invention will become better understood with regard to the following description, appended claims, and drawings where:

Figure 7:
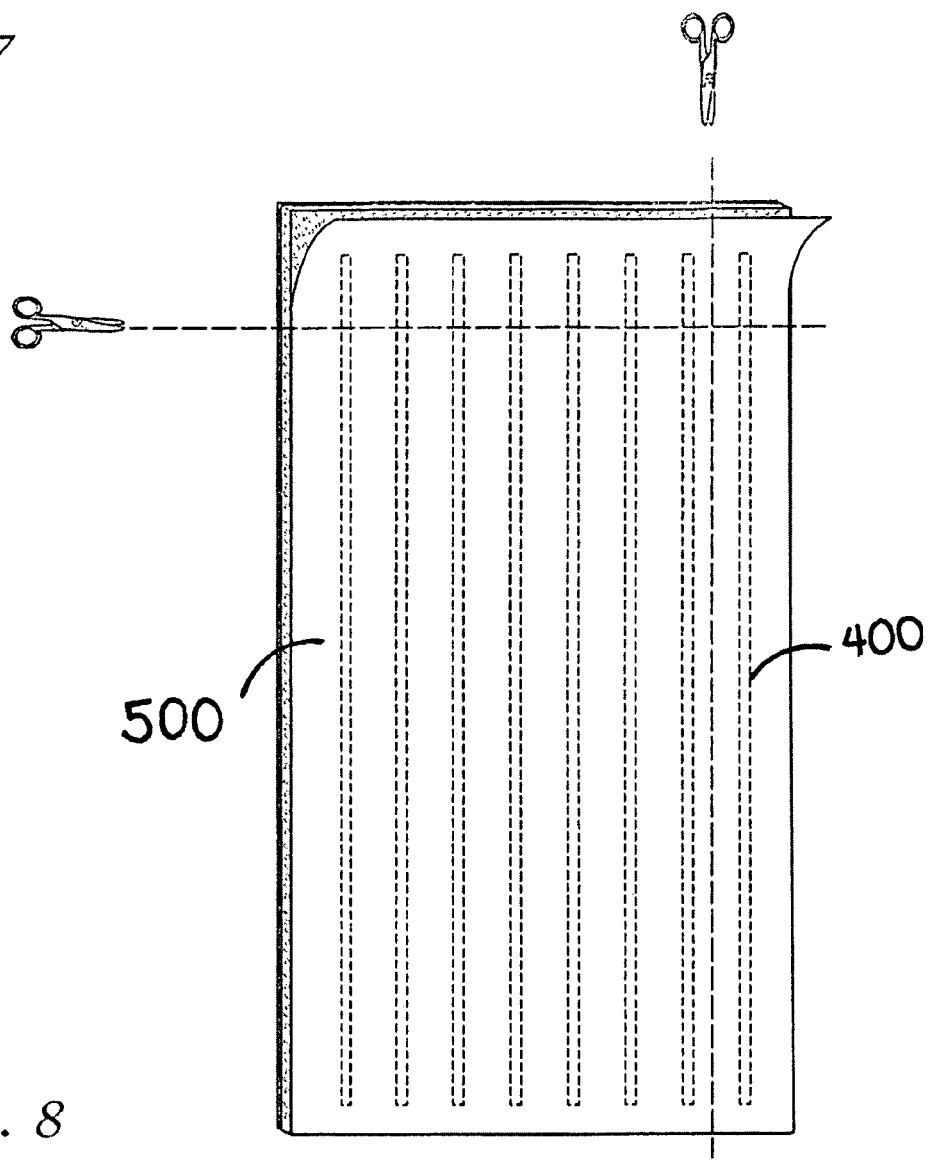
Figure 8:
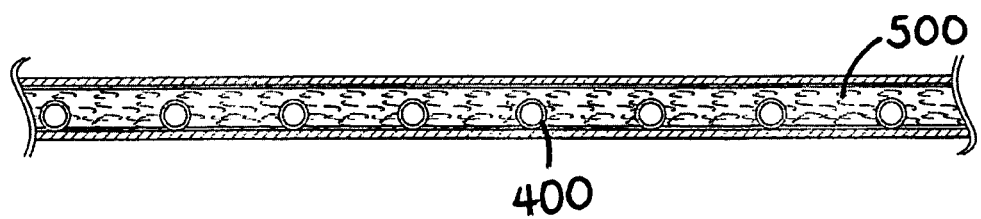
Figure 9:
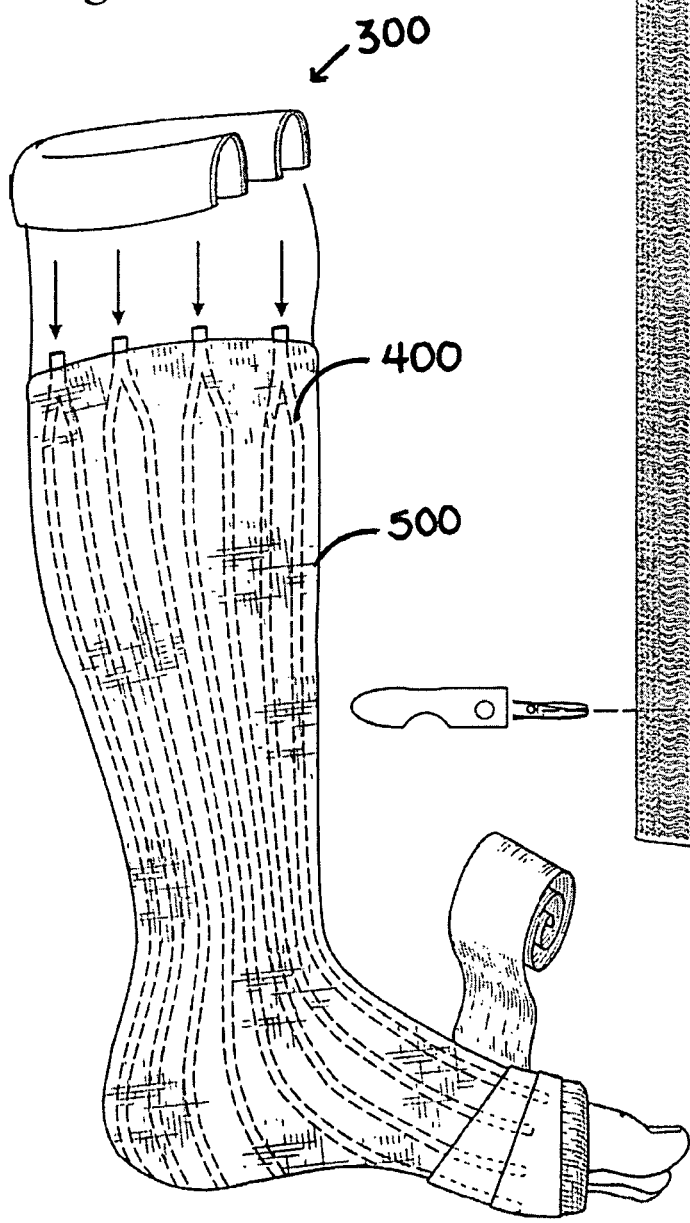

FIG. 5A-B show perspective views of a portable fluid flow manipulation device;

FIG. 6 shows a cross sectional view of the portable fluid flow manipulation device;

FIG. 7 shows a perspective view of another embodiment of the present invention;

FIG. 8 shows is a cross sectional view of the embodiment shown in FIG. 7;

FIG. 9 shows yet another embodiment of the present invention; and

Figure 10:
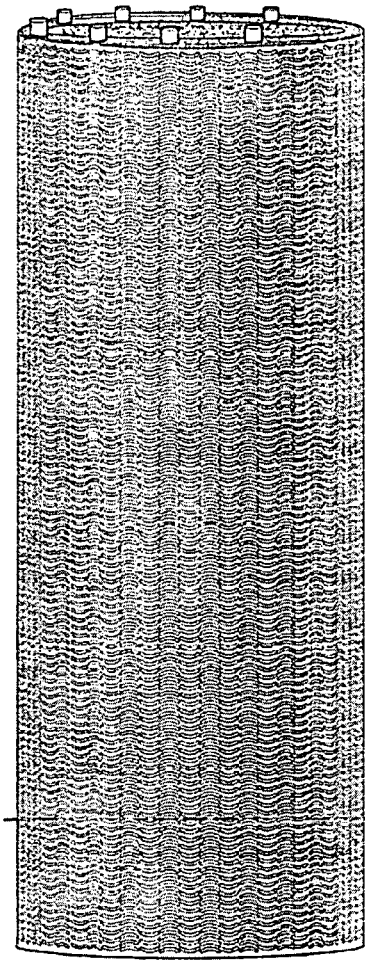

FIG. 10 shows a perspective view of the embodiment shown in FIG. 9.

DESCRIPTION

As Seen in FIGS. 1-6, a portable cast ventilating system 100 adapted for use on a cast 110, the system 100 comprises of a portable fluid flow manipulation device 200, a manifold collar 300 operatively connected to the portable fluid flow manipulation device 200, and at least one tube 400 operatively connected to the manifold collar 300.

As seen in FIGS. 1, 5A, 5B, and 6, the portable fluid flow manipulation device 200 has at least one fluid flow manipulation intake element 210. At least one fluid flow control element 212, the fluid flow control element 212 is housed within the fluid flow manipulation device 200 and the fluid flow control element 212 operatively connects to each fluid flow manipulation intake element 210. A manipulation outflow valve 214, the manipulation outflow valve 214 operatively connects to the fluid control element 212. And, a rechargeable power source 216, the rechargeable power source 216 operatively connects to the fluid flow control element 212.

As seen in FIGS. 1, 3A, 3B, 4, and 9 the manifold collar 300 defines an intake fluid flow collar valve 310 and at least one outflow fluid flow collar valve 312. The manifold collar 300 is configured so that each outflow fluid collar valve 312 is positioned within a cast. The intake fluid flow collar valve 310 operatively connects to the manipulation outflow valve 214.

Figures 1, 2:
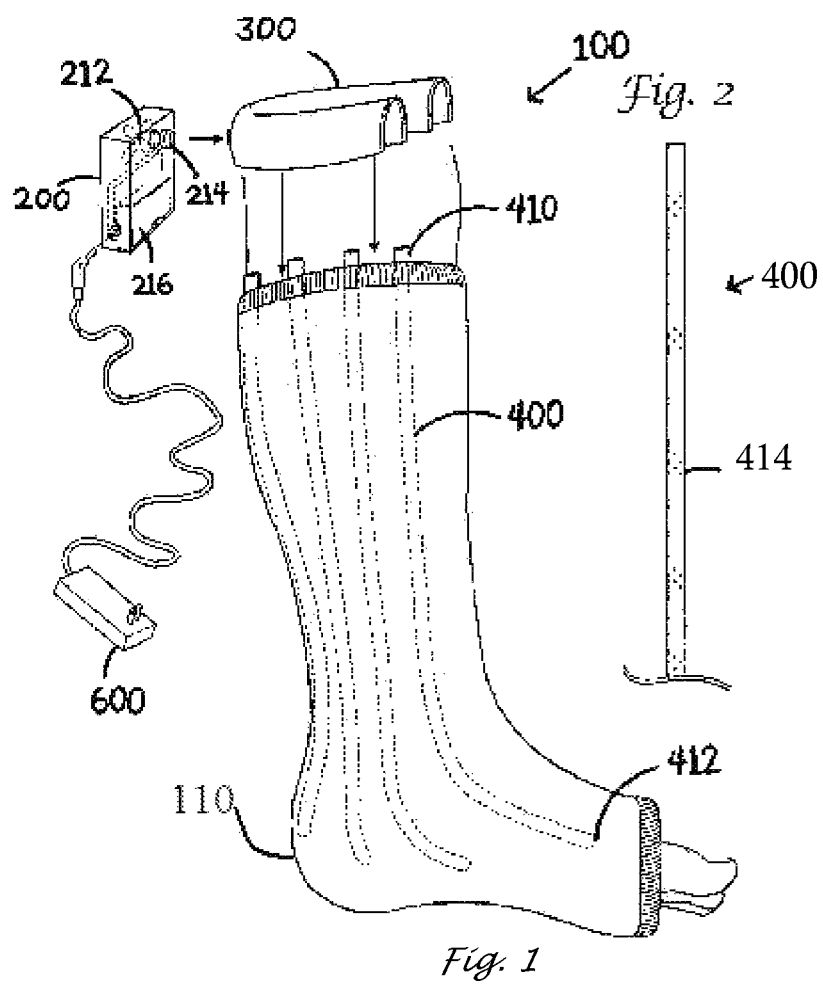
FIG. 1 shows a side view of the present invention.
FIG. 2 shows a side view of a portion of a tube used with the present invention.
Figure 3A:
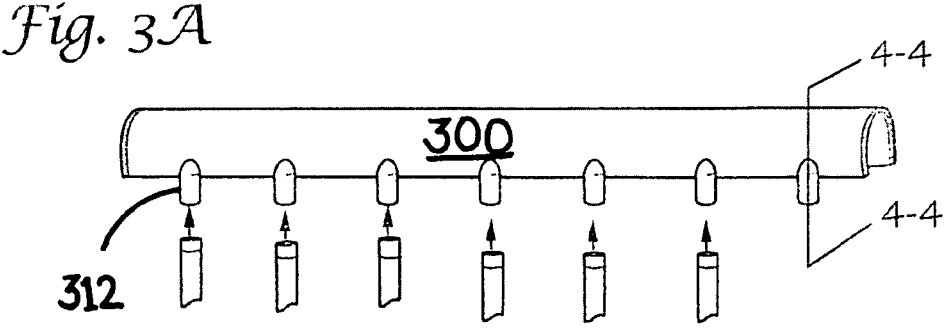
FIG. 3A shows a perspective view of a manifold of the present invention, the view shows the interior side of the manifold.
Figure 3B:
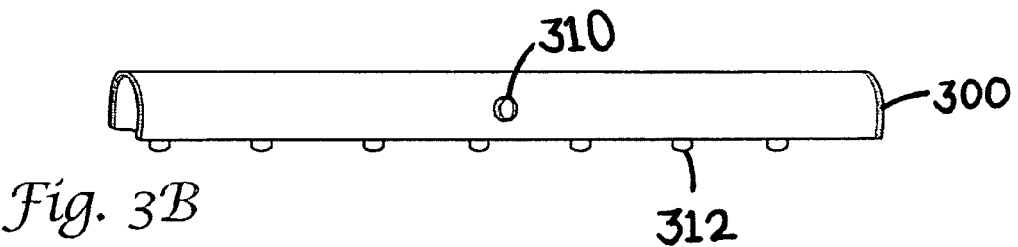
FIG. 3B shows a perspective view of a manifold of the present invention, the view shows the exterior side of the manifold.
Figure 4:
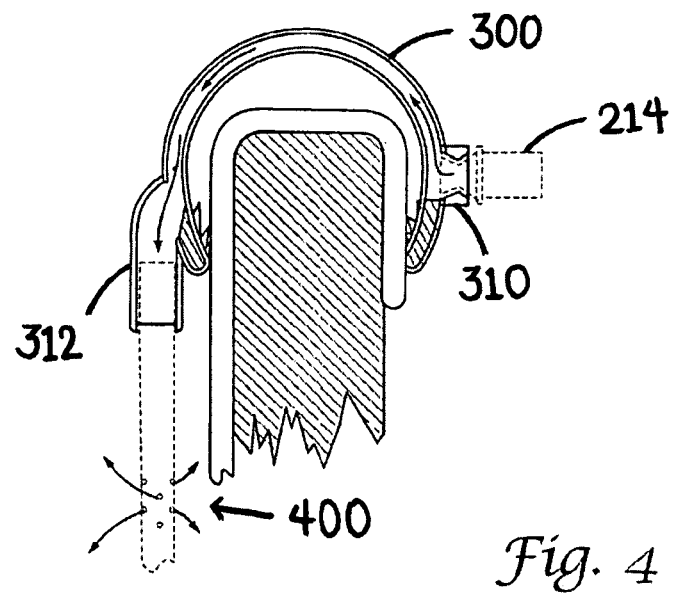
FIG. 4 shows a cross sectional view of the manifold, the manifold is mounted on a cast.

As seen in FIGS. 1-2, each tube 400 has a first 410 and a second end 412. The first end of each tube 410 attaches to each outflow fluid collar valve 312, the second end of each tube 412 is sealed, and each tube 400 defines a plurality of vents 414.

As seen in FIGS. 1 and 6, in an embodiment of the present invention, the portable cast ventilating system 100 might further comprise of a removable and rechargeable heat transfer element 218. The heat transfer element 218 is housed within the manipulation device 200 and the heat transfer element 218 operatively connects to each fluid flow manipulation intake element 210 and to each fluid flow control element 212. The removable heat transfer element 218 might comprise of at least one heat retention cell.

As seen in FIGS. 7-10, in another embodiment of the present invention, the portable cast ventilating system might further comprise of a gauze 500 and each tube 400 is embedded within the gauze 500 at a predetermined position. The gauze 500 might be antimicrobial.

As seen in FIG. 6, in yet another embodiment of the present invention, the power source might be a rechargeable battery 216.

As seen in FIG. 1, in still a further embodiment of the present invention, the portable cast ventilating system 100 might further comprise of a power adapter 600. The power adapter 600 operatively connects to the rechargeable battery 216.

The portable and rechargeable cast ventilating system 100 adapted for use on casts is used in the following manner. First, by providing the portable and rechargeable cast ventilating system 100. Then, providing a user having a cast over a specific part of the user's body. Next, inserting each tube 400 of the portable cast ventilating system within the cast. Then, attaching the manifold collar 300 of the portable cast ventilating system to the cast so that each tube 400 operatively connects to each outflow fluid flow collar valve 312. Next, attaching the portable fluid flow manipulation device 200 to the manifold collar 300 so that the intake fluid collar valve 310 of the collar valve 300 operatively connects to the manipulation outflow valve 214 of the portable fluid flow manipulation device 200. And lastly, energizing the fluid flow control element 212 of the portable and rechargeable cast ventilating system 100.

An advantage of the present invention is that it provides a portable and rechargeable cast ventilating system adapted for use on casts that allows users of the system to carry out their normal tasks without having to have the system plugged in.

Another advantage of the present invention is that it provides a portable and rechargeable cast ventilating system adapted for use on casts that allows a user to control the temperature of the fluid flow delivered to the areas of the user being covered by the cast.

A further advantage of the present invention is that it provides a portable and rechargeable cast ventilating system adapted for use on casts that can be recharged while the user of the system is using the cast.

Still a further advantage of the present invention is that it provides a portable and rechargeable cast ventilating system that allows a user to minimize the normal odors accumulated within a cast due to use.

Although the present invention has been described in considerable detail with reference to certain preferred versions thereof, other versions are possible. Therefore, the spirit and the scope of the claims should not be limited to the description of the preferred versions contained herein.

What is claimed is:

1. A portable and rechargeable cast ventilating system adapted for use on casts, the system comprising:
   a portable fluid flow manipulation device comprising a heat transfer element, at least one fluid flow manipulation intake element, at least one fluid flow control element housed within the fluid flow manipulation device, the fluid flow control element operatively connects to each fluid flow manipulation intake element, a manipulation outflow valve that operatively connects to the fluid control element, and a rechargeable power source, the rechargeable power source operatively connects to the fluid flow control element;
   a manifold collar comprising an intake fluid flow collar valve to directly and removably receive the manipulation outflow valve of the manipulation device and at least one outflow fluid flow collar valve, the manifold collar is configured so that each outflow fluid collar valve is positioned within a cast, wherein the intake fluid collar valve directly and removably connects to the manipulation outflow valve; and
   at least one tube, each tube having a first and a second end, the first end of each tube attaches to each outflow fluid collar valve, the second end of each tube is sealed, and each tube defines a plurality of vents;
   wherein the heat transfer element is removably housed within the manipulation device that operatively connects to each fluid flow manipulation control element, wherein the removable heat transfer element comprises at least one heat retention cell.

2. The portable cast ventilating system of claim 1, wherein the removable heat transfer element is powered by the rechargeable power source that is rechargeable while in use powering the removable heat transfer element.

3. The portable cast ventilating system of claim 2, further comprising a gauze and each tube is embedded within the gauze at a predetermined position.

4. The portable cast ventilating system of claim 3, wherein the gauze is antimicrobial.

5. The portable cast ventilating system of claim 4, wherein the rechargeable power source is a rechargeable battery.

6. The portable cast ventilating system of claim 5, further comprising a power adapter, the power adapter operatively connects to the rechargeable battery.

7. The portable cast ventilating system of claim 2, wherein the rechargeable power source is a rechargeable battery.

8. The portable cast ventilating system of claim 7, further comprising a power adapter, the power adapter operatively connects to the rechargeable battery.

9. The portable cast ventilating system of claim 1, wherein the at least one tube is adapted to be at least partially located adjacent to skin of a user.

10. The portable cast ventilating system of claim 1, wherein the manipulation outflow valve is removably insertable into the intake fluid flow collar valve on the manifold collar to directly and removably connect the fluid flow manipulation device to the manifold collar.

11. A portable cast ventilating system adapted for use on casts, the system comprising:
    a portable fluid flow manipulation device comprising at least one fluid flow manipulation intake element, a removable and rechargeable heat transfer element with at least one heat retention cell, the heat transfer element is housed within the manipulation device, each fluid flow manipulation intake element operatively connects to the heat transfer element, at least one fluid flow control element, the fluid flow control element housed within the fluid flow manipulation device, the fluid flow control element operatively connects to the heat transfer element, a manipulation outflow valve, the manipulation outflow valve operatively connects to the fluid control element, and a rechargeable power source, the rechargeable power source operatively connects to the fluid flow control element;

a manifold collar comprising an intake fluid flow collar valve to directly and removably receive the manipulation outflow valve of the manipulation device and at least one outflow fluid flow collar valve, the manifold collar is configured so that each outflow fluid collar valve is positioned within a cast, wherein the intake fluid collar valve directly and removably connects to the manipulation outflow valve; and at least one tube being at least partially locatable adjacent to skin of a user, each tube having a first and a second end, the first end of each tube attaches to each outflow fluid collar valve, the second end of each tube is sealed, and each tube defines a plurality of vents.

12. The portable cast ventilating system of claim 11, further comprising a gauze and each tube is embedded within the gauze at a predetermined position.

13. The portable cast ventilating system of claim 12, wherein the gauze is antimicrobial.

14. The portable cast ventilating system of claim 13, wherein the rechargeable power source is a rechargeable battery.

15. The portable cast ventilating system of claim 14, further comprising a power adapter, the power adapter operatively connects to the rechargeable battery.

16. The portable cast ventilating system of claim 12, wherein the rechargeable power source is a rechargeable battery.

17. The portable cast ventilating system of claim 16, further comprising a power adapter, the power adapter operatively connects to the rechargeable battery.

* * * * *